United States Patent [19]

Rijkers et al.

[11] Patent Number: 5,502,238
[45] Date of Patent: Mar. 26, 1996

[54] PROCESS FOR THE CRYSTALLIZATION OF ASPARTAME

[75] Inventors: Marinus P. W. M. Rijkers, Stein; Alexander P. M. Vrinzen, Meerssen, both of Netherlands

[73] Assignee: Holland Sweetener Company V.o.F., Netherlands

[21] Appl. No.: 396,861

[22] Filed: Mar. 1, 1995

Related U.S. Application Data

[63] Continuation of Ser. No. 102,217, Aug. 5, 1993, abandoned.

[30] Foreign Application Priority Data

Aug. 5, 1992 [NL] Netherlands ............................. 9201408

[51] Int. Cl.$^6$ ................................................. C07C 229/02
[52] U.S. Cl. .................................................................. 560/41
[58] Field of Search .................................................. 560/41

[56] References Cited

U.S. PATENT DOCUMENTS

| | | |
|---|---|---|
| 4,656,304 | 4/1987 | Oppici et al. |
| 5,041,607 | 8/1991 | Naruse et al. |
| 5,097,060 | 3/1992 | Naruse et al. |
| 5,248,806 | 9/1993 | Kishimoto et al. |
| 5,266,719 | 11/1993 | Kishimoto et al. |

Primary Examiner—José G. Dees
Assistant Examiner—Samuel Barts
Attorney, Agent, or Firm—Cushman Darby & Cushman

[57] ABSTRACT

The invention relates to a process for the crystallisation of aspartame by neutralising an aqueous solution of aspartame, having a pH of less than 3, with a base and homogenising the solution by means of forced convection, characterised in that the solution is neutralised, and homogenised, in such a manner that the solution obtained is substantially homogeneous and has a pH higher than 3, with the solution no longer being mechanically stirred at least from the beginning of the last second before crystallisation is visually perceptible.

30 Claims, No Drawings

PROCESS FOR THE CRYSTALLIZATION OF ASPARTAME

This is a continuation of application Ser. No. 08/102,217, filed on Aug. 5, 1993, now abandoned.

The invention relates to a process for the crystallisation of aspartame by neutralising an aqueous solution of aspartame, having a pH of less than 3, with a base and homogenising the solution by means of forced convection.

Aspartame is a sweetener which is used extensively in low-calorie products such as cold drinks. Mostly, aspartame is crystallised, after its preparation, from water or, if desired, from water containing up to 20% by weight of methanol or ethanol. In various commercially used processes of preparation of aspartame, it is in the first instance crystallised out as the aspartame.HCl salt. This salt is then recrystallised by neutralising the acid solution and then, if appropriate, cooling it, as described, for example, in U.S. Pat. No. 4,618,695. This can, for example, be carried out in suspension, as described in U.S. Pat. No. 4,778,916, or by preparing a homogeneous solution at an elevated temperature and neutralising it, with stirring, and cooling it, as described, for example, in U.S. Pat. No. 4,677,222 and U.S. Pat. No. 4,656,304. The neutralisation can, for example, also be carried out by adding alkali dropwise to a solution, as described in EP-A-187.530 and U.S. Pat. No. 4,918,216.

Aspartame has a relatively low solubility in water, so that the crystallisation yield per liter of solution is rather low. For example, in order to crystallise out 40 g of aspartame, it is necessary to cool one liter of aqueous solution, containing 4.8% by weight of aspartame, from 60° to 5° C. Given that relatively large quantities of water must be cooled in this procedure, aspartame is preferably produced in a stirred crystalliser. A stirred cooling crystalliser has the advantage that heat can be removed relatively efficiently.

However, stirred crystallisation of aspartame has the disadvantage that the crystals formed have a relatively high specific cake resistance. This means that, after crystallisation, the aspartame slurry can generally only be filtered rather laboriously.

EP-A-091.787 proposes allowing aspartame to crystallise by cooling under static conditions (without stirring). Inherently, larger crystals are obtained by means of this process than in stirred crystallisation, but the cooling efficiency in a non-stirred solution is relatively low, so that a relatively large heat exchanging surface area is needed and the crystallisation takes a relatively long time.

The object of the invention is to provide a process for the crystallisation of aspartame, whereby relatively large crystals having a low specific cake resistance are obtained, and whereby the time-consuming cooling stage under static conditions is dispensed with.

According to the invention, this object is achieved in that the acid aspartame solution is neutralised and homogenised in such a manner that the solution obtained is substantially homogeneous and has a pH higher than 3, with the solution no longer being mechanically stirred at least from the beginning of the last second before crystallisation is visually perceptible. In this context mechanical stirring means that the system is exposed to forced convection by mechanical means such as stirrers, pumps and the like. As soon as these mechanical means have been stopped there is no longer forced convection in the sense of the present patent application.

The pH of a solution means the pH of a particular solution measured at the respective temperature with the aid of a pH-meter device type Knick Portamess 752, the actual pH value measured at that temperature being automatically corrected to the pH value at a standard temperature of 20° C. In the present patent application the latter value is always used where pH is mentioned.

The pH of the solution before neutralisation is lower than 3 but as a rule higher than 0.5, preferably higher than 1 and in particular higher than 1.5. An excessively low pH promotes the decomposition of aspartame and is therefore undesirable. The optimum solubility is at a pH of about 2.3. The pH is thus preferably lower than 2.9, in particular lower than 2.5. The pH is critical only in connection with the solubility of aspartame. At too high a pH, the solubility of aspartame may be so low that (undesirable) crystallisation may already occur.

Very suitable acids for attaining a pH< 3 are hydrochloric acid, sulphuric acid, phosphoric acid or nitric acid. The use of hydrochloric acid or sulphuric acid is preferred, and that of hydrochloric acid particularly so. The concentration of the acid is not critical but will, for economic reasons, be above 1N. In general, a saturated solution or a solution of between 5 and 12N will be chosen. However, it is also possible to pass HCl gas through the solution which is to be acidified. It is also possible to start from a salt of aspartame, such as, for example, the HCl salt, the sulphuric acid salt or the phosphoric acid salt.

The amount of aspartame in the solution before crystallisation is as a rule between 1.5 and 20% by weight. Preferably, the amount of aspartame in the solution is more than 3% by weight. % by weight of aspartame means the amount of aspartame calculated as free aspartame. The solubility of the salts of aspartame, or of aspartame in an acid medium, is substantially greater than that of the neutralised aspartame, and a man skilled in the art can readily determine the concentrations at which no crystallisation will result in the solution prior to neutralisation.

Preferably, the concentration is so chosen that after neutralisation more than 1% by weight of supersaturation, in particular more than 1.5% by weight, but as a rule less than 15% by weight, preferably less than 8% by weight, of supersaturation results. The supersaturation is here expressed as the absolute supersaturation in % by weight of aspartame. Excessively high supersaturation can yield small crystals which have less good filtration characteristics. High supersaturation, however, makes an important contribution towards a relatively high yield per unit of volume.

The aqueous solution can contain a minor amount, that is to say up to 25% by weight, of a lower alcohol having 1–4 C-atoms, such as, for example, ethanol or methanol.

The solution of aspartame having a pH of less than 3 is thereafter brought to a pH higher than 3 by means of a base. Preferably, the amount of base added is such that a pH higher than 4 but less than 8 is obtained. In particular, the amount of base added is such that a pH of between 4 and 7, more particularly between 4 and 6, is obtained.

The base used is preferably an aqueous alkali solution, in particular of sodium hydroxide, potassium hydroxide, sodium carbonate, sodium bicarbonate, ammonium hydroxide or ammonium carbonate. As a rule, a solution of more than 0.1N, preferably more than 0.2N, will be used. A low concentration of base in the aqueous alkali solution is of advantage if the man skilled in the art wishes to mix two streams of approximately equal volume. For economic reasons, however, a solution of more than 1N or a saturated solution of a base will frequently be used, so that less liquid has to be filtered and a higher yield is obtained. Preferably, an aqueous solution of sodium hydroxide or ammonium hydroxide is used. However, it is also possible to use a base as a solid, by mixing a very readily soluble base such as NaOH, in a very finely divided state, with the aspartame solution to be neutralised. In order to avoid undesirable decomposition into diketopiperazine at high pH the homogenising in such a case has to be carried out as quickly as possible. It is also possible to use gaseous ammonia as the base.

In the process according to the invention, the base is added in a very short time to the aspartame solution to be neutralised. The forced convection required in order to mix the base rapidly with the aspartame solution should take only such a short time that there is an interval of at least one second between the instant at which the solution is no longer exposed to this forced convection and the occurrence of visually perceptible start of crystallisation. This interval is preferably at least 3 and particularly preferentially at least 4 seconds.

Such a process of homogenisation means (within the scope of the present patent application) that the means which bring about the forced convection are stopped at least 1 second and preferably at least 3 seconds before the start of crystallisation occurs, or that the solution is treated in such a way that substantially no forced convection occurs any more. The latter case will apply in particular in continuous crystallisation, such as for instance in a plug flow crystallisation process through a pipe. As a rule after stopping the mechanical means convection will still occur for some time before the solution has come completely to rest. This is, however, not of essential importance for the process according to the invention, nor is this considered to be forced convection.

The instant of the visually perceptible start of crystallisation depends on numerous factors such as, amongst others, the degree of supersaturation and the temperature of the solution. For example, at 4% by weight of supersaturation there is less time available for mixing than at 2% by weight supersaturation.

The start of crystallisation is easily determined visually in a glass vessel, wherein an experiment according to the invention can be carried out. It is also possible to use techniques such as light-scattering, for example using a laser, for determining the start of crystallisation. The start time is defined as the time from addition of the total amount of the base to when the first crystallisation is visually perceptible. This start time is unexpectedly long, given the degree of supersaturation. The presence of other components in the solution, such as impurities or additives— such as salt(s)—can influence the start time.

Preferably, the start time is so chosen, through choice of temperature and degree of supersaturation, that it is at least 10 seconds. It is then in particular easily possible to neutralise and homogenise the acid aspartame solution and thereafter to allow the solution to crystallise without forced convection.

If desired, a longer start time can also be employed, in particular by choosing a higher temperature of the aspartame solution. Thus, in an aspartame solution at 60° C. and 3% by weight of supersaturation, crystallisation start is visually perceptible only after 60–120 seconds.

Mixing the aspartame solution with the base preferably takes place in a static mixer, through which the liquid streams to be mixed are pumped. Other apparatus, known to the man skilled in the art, for rapidly mixing two liquids (or one liquid and one solid or gas to be dissolved rapidly therein) can also be used. The mixing may be carried out as a continuous or discontinuous process.

Though it is in particular important that the homogenisation of the aspartame solution (by means of forced convection) for the purpose of neutralisation should be completed before the start of crystallisation occurs (which start may not be perceptible for up to 120 seconds), it is preferable that homogenisation should not be allowed to take longer than 10, more particularly not longer than 5, seconds.

Directly after mixing, the neutralised aspartame solution is run into a vessel which is, if desired, provided with baffles in order to minimise the convection of the solution as rapidly as possible, and aspartame is crystallised out of the solution under static conditions. Since, by means of the present process, the crystallisation is very rapidly virtually complete (at a given temperature), it is also readily possible to carry out the crystallisation continuously in a tubular vessel through which the solution to be crystallised is pumped at a very low speed.

As described above, various processes are known wherein an aspartame.HCl salt is obtained (see U.S. Pat. No. 4,628,695, U.S. Pat. No. 4,778,916, U.S. Pat. No. 4,677,222 and EP-A-187.530). The process according to the invention is very suitable for rapidly crystallising such a salt, giving very pure aspartame and a slurry which is readily filtered.

However, it is also possible to prepare aspartame as a neutral compound from a precursor containing a protective group, as, for example, described in U.S. Pat. No. 3,786,039 or U.S. Pat. No. 4,282,721.

For aspartame obtained in such a manner, the process according to the invention can be used very advantageously because the solution obtained, after acidification to a pH of less than 3, can be cooled very efficiently as a solution, after which a crystallisation process according to the invention can be employed. In this first preferred embodiment a neutral aspartame solution containing more than 1.5% by weight of aspartame and preferably more than 3% by weight of aspartame is brought to a pH of less than 3 by means of an acid, at a temperature above 50° C., preferably at a temperature between 50° C. and 80° C., in particular between 55° C. and 70° C., and the solution is cooled at least 10° C. under forced convection conditions. In doing so, the concentration, temperature and pH are so chosen that no aspartame crystallises out. Preferably, the solution is cooled at least 30° C., in particular about 40° C. However, at high aspartame concentration it may suffice to use a shorter cooling range of, for instance, 20° C. Analogously to this first preferred embodiment of acidifying in a neutral solution it is of course also possible to dissolve aspartame in, preferably warm, water which is already acidified. Thus using the process according to the invention—it is possible to obtain crystalline aspartame of very high purity in a very advantageous way from crystalline aspartame which still contains an undesirably high amount of impurities.

Subsequently, the cooled solution is brought to a pH of above 3 by means of a base under forced convection. Thereafter, before crystallisation starts, the means which bring about said forced convection are stopped and the aspartame is crystallised out under static conditions.

The warm solution can be cooled in a manner known per se. Preferably a through-flow heat exchanger is used, whereby the heat is removed efficiently.

The temperature in the cooled acid solution is as a rule below 40° C., but may also—when an acid solution having a high temperature and concentration is started from—be higher, up to 70° C. It is not economically advantageous to cool the solution further than to 5° C. Preferably, the solution is cooled to 5°–35° C. A low temperature has the advantage that it counteracts the growth of microorganisms. However, a high temperature has the advantage of a longer time until crystallisation starts. It was also found, unexpectedly, that at a higher temperature crystals having very good filtration characteristics can be obtained at higher supersaturation.

In a further preferred embodiment of the process according to the invention an aspartame.HCl salt is dissolved. Such a solution has a pH of about 1.5–1.8. If desired, the solution can be brought to a different pH between 1 and 3. It can be advantageous to dissolve the aspartame salt at a temperature of between 20° and 80° C. (in order to increase the rate of dissolution) and then to cool the acid solution (to improve the crystallisation efficiency).

After the crystallisation, which as a rule lasts from 2 minutes to 2 hours, preferably between 5 and 30 minutes, the mass obtained is—if desired after mechanically breaking up the pseudo-solid phase which may be obtained—run into a liquid-solid separator, for example a filter centrifuge or a belt filter. It is, however, also possible to cool the mass further in a crystalliser under forced convection. This is particularly of advantage if the aspartame solution has been neutralised at a temperature above 15° C. and in particular at 25°–40° C. In the course of this last stirred crystallisation step—if employed—the aqueous crystal mass is then cooled to below 25° C., preferably below 20° C. and in particular to a temperature of 5°–15° C.

After completion of the crystallisation the crystals are, as already mentioned, separated from the water, for example by filtration or centrifuging. The wet crystal mass which results is then preferably washed with cold demineralised water. The mass obtained after filtration and washing as a rule consists of aspartame with 25–50% by weight of water. Thereafter, this wet aspartame cake is further dried, in a manner known per se, to a moisture content of 1–6% by weight.

The invention will be explained further with reference to the non-limiting examples which follow.

In the examples, the specific cake resistance R (m/kg) and the characteristic particle size (μm) of the slurries obtained are given.

Filtration tests were carried out using a filter having a surface area of 19.64 cm². The filtrate was collected in a vessel, the weight of which was continuously determined by means of a recorder. The pressure difference for the filtration of the slurry was obtained by applying controlled excess pressure on the slurry.

The specific cake resistance was calculated from formula I.

$$\frac{t}{V} = \frac{R \cdot \eta \cdot C}{2 \cdot \Delta P \cdot A^2} V + \frac{Rm \cdot \eta}{\Delta P \cdot A} \quad (s/m^3) \qquad I$$

t= Filtration time (s)
V= Filtrate volume (m³)
R= Specific cake resistance (m/kg)
η= Dynamic viscosity of the filtrate (Pa.s)
ΔP= Pressure difference across the filter and the filter cake (Pa)
C= Weight of the precipitated crystals per unit of volume of the filtrate obtained (kg/m³)
Rm= Filter resistance (l/m)
A= Filter surface area (m²)

The characteristic diameter $D_{ch}$ is calculated according to formula II $$\pm \mu \quad D_{ch} = \frac{V^2 \cdot 360 \cdot \eta \cdot C}{t \cdot A^2 \cdot \Delta P} \quad 1/2 \qquad II$$

wherein the symbols have the abovementioned meaning; ΔP is $10^5$ Pa.

Stirred crystallisation of aspartame gives a specific cake resistance (R) greater than $6.10^{10}$ m/kg and a characteristic diameter ($D_{ch}$) of about 3 μm. Using the process according to the invention, values of R of between $5.10^8$–$4.10^{10}$ m/kg and of $D_{ch}$ of 4–20 μm can be achieved very advantageously by means of a rapid crystallisation.

Preferably, the process according to the invention is carried out in such a manner—which a man skilled in the art can determine in a simple manner with the aid of the present patent application—that an aspartame slurry having a specific cake resistance as defined above of less than $1.10^{10}$ m/kg, in particular $1.10^8$–$8.10^9$ m/kg, is obtained. The characteristic diameter is preferably greater than 5 μm, in particular between 7 and 25 μm.

EXAMPLES I–VII

A 3.9% by weight aspartame solution was prepared from 1 liter of water at 60° C., and aspartame, in a 1.75 liter glass vessel provided with a stirrer and baffles. For each example, a calculated quantity of 37% by weight HCl solution was always metered into the one liter of solution so that undersaturated solutions were obtained after cooling to the temperature specified in Table 1.

Thereafter, an acid aspartame solution was each time neutralised with a calculated quantity of 37% by weight NaOH solution, using good stirring (300 rpm). The solution was stirred for 5 seconds (the theoretically required mixing time was 3 seconds), after which the stirrer was stopped. 1 to 10 seconds thereafter, crystallisation start was visually perceptible. After 15 minutes, the slurry was equilibrated by stirring it for 15 minutes with a stirring speed of 300 rpm. Thereafter, the filtration characteristics of the slurries obtained were measured. The results are shown in Table 1.

TABLE 1

| Example | I | II | III | IV | V | VI | VII |
| --- | --- | --- | --- | --- | --- | --- | --- |
| Starting solution | | | | | | | |
| Metered-in HCl[1] (g) | 3.02 | 3.06 | 3.75 | 4.55 | 4.52 | 3.93 | 4.08 |
| pH | 2.8 | 2.9 | 2.7 | 2.6 | 2.4 | 2.4 | 2.4 |
| Temp (°C.) | 30 | 30 | 25 | 20 | 15 | 10 | 5 |
| Neutralised solution | | | | | | | |
| Metered-in NaOH[1] (g) | 3.31 | 3.74 | 4.33 | 5.18 | 5.00 | 4.58 | 4.68 |
| pH | 4.2 | 5.5 | 4.6 | 4.7 | 4.4 | 5.5 | 5.7 |
| Temp (°C.) | 31 | 31 | 26 | 21 | 16 | 11 | 6 |

TABLE 1-continued

| Example | I | II | III | IV | V | VI | VII |
|---|---|---|---|---|---|---|---|
| Crystallisation | | | | | | | |
| Supersaturation[2] (%) | 2.5 | 2.5 | 2.7 | 2.9 | 3.1 | 3.2 | 3.4 |
| Crystal start time (s) | 15 | 10 | 10 | 10 | 10 | 6 | 8 |
| Time after stopping stirrer (s) | 10 | 5 | 5 | 5 | 5 | 1 | 3 |
| Filtration characteristic | | | | | | | |
| R[3] (m/kg) | 2.6E9 | 1.7E9 | 3.7E9 | 9.2E9 | 1.8E10 | 4.1E10 | 4.0E10 |
| $D_{ch}$[4] (µm) | 10.4 | 10.0 | 8.7 | 6.2 | 4.5 | 3.5 | 3.4 |

[1]quantity expressed as g of 100% strength material
[2]absolute supersaturation in % by weight of aspartame
[3]specific cake resistance
[4]characteristic diameter

COMPARATIVE EXPERIMENT A AND EXAMPLES VIII–XIII

Experiments, as shown in Table 2, were carried out analogously to Examples I–VII. In comparative experiment A the stirrer was not stopped. The stirrer thus remained running for 0.5 hour.

In Example VIII the stirrer was stopped after 2 seconds. Although the mixing time was 3 seconds, the solution nevertheless appeared sufficiently homogeneous to give good results.

In Example XI, the slurry obtained at 30° C. was cooled further under forced convection. The table gives the filtration characteristic of the ultimately obtained slurry, which was very easy to filter.

The tests show that a slurry with good filtration characteristics is easily obtainable by crystallisation at a higher temperature (higher than 25° C.).

TABLE 2

| Example | A | VIII | IX | X | XI[1] | XII[2] | XIII[2] |
|---|---|---|---|---|---|---|---|
| Starting solution | | | | | | | |
| Metered-in HCl (g) | 4.0 | 4.8 | 4.8 | 4.0 | 3.1 | 5.8 | 5.0 |
| pH | 2.5 | 1.9 | 1.8 | 2.3 | 2.8 | 2.7 | 2.7 |
| Temp (°C.) | 10 | 10 | 10 | 10 | 30 | 50 | 55 |
| Neutralised solution | | | | | | | |
| Metered-in NaOH (g) | 4.4 | 5.3 | 5.3 | 4.4 | 3.4 | 6.4 | 5.5 |
| pH | 4.2 | 4.2 | 4.2 | 4.2 | 4.3 | 4.0 | 4.1 |
| Temp (°C.) | 11 | 11 | 11 | 11 | 31 | 52 | 57 |
| Crystallisation | | | | | | | |
| Supersaturation (%) | 3.2 | 3.2 | 3.2 | 3.2 | 2.4 | 4.4 | 3.8 |
| Crystal start time (s) | 9 | 12 | 12 | 8 | 9 | 6 | 10 |
| Time after stopping stirrer (s) | X | 10 | 7 | 3 | 4 | 1 | 5 |
| Filtration characteristic | | | | | | | |
| R (m/kg) | 6.6E10 | 3.2E10 | 4.0E10 | 4.0E10 | 2.4E9 | 7.4E8 | 1.3E9 |
| $D_{ch}$ (µm) | 3.3 | 3.9 | 3.4 | 3.5 | 12.0 | 19.3 | 14.8 |

[1]In this example, the slurry obtained at 30° C. was cooled further, with stirring, to 10° C., in the course of which further crystallisation occurred. R and $D_{ch}$ are measured after further cooling.
[2]Examples XII and XIII start from an 8% aspartame solution which was prepared by dissolving aspartame, at 60° C., in water which already contained the amount of HCl shown in the table.

We claim:

1. A process for the crystallization of aspartame comprising the following steps:

neutralizing with a base an acidic solution of aspartame in water having a pH less than about 3 to obtain a neutralized solution having a pH greater than about 3, wherein said neutralization is rapidly effected;

mixing said acidic solution during said neutralization to obtain a substantially homogeneous solution, wherein said mixing is rapidly effected; and stopping said mixing at least one second before crystallization becomes visually perceptible; and thereafter crystallizing aspartame from the mixed solution obtained in the previous step at a substantially constant temperature, wherein the temperatures of said acidic and neutralized solutions during said neutralization and crystallization steps are not more than about 5° C. different.

2. A process according to claim 1, wherein said mixing is conducted for up 120 seconds.

3. A process for the crystallization of aspartame comprising the following steps:

rapidly neutralizing an acidic solution of aspartame in water having a pH less than about 3 with a base to obtain a neutralized solution having a pH greater than about 3;

rapidly mixing said acidic solution during said neutralization to obtain a substantially homogeneous solution; and stopping said mixing at least one second before crystallization becomes visually perceptible; and thereafter crystallizing aspartame from the mixed solution obtained in the previous step at a substantially constant temperature.

4. A process according to claim 3, wherein said acidic solution has a pH higher than about 0.5.

5. A process according to claim 3, wherein the concentration of aspartame in said acidic solution is between about 1.5 and about 20% by weight.

6. A process according to claim 3, wherein after neutralization, an absolute supersaturation of about 1–15% by weight of aspartame is achieved.

7. A process according to claim 6, wherein after neutralization, an absolute supersaturation of about 1–8% by weight of aspartame is achieved.

8. A process according to claim 3, wherein said acidic solution is neutralized with an aqueous alkali solution.

9. A process according to claim 8, wherein said alkali solution is an aqueous solution of sodium hydroxide, potassium hydroxide, sodium carbonate, sodium bicarbonate, ammonium carbonate or ammonium hydroxide.

10. A process according to claim 3, wherein said mixing is stopped at least about three seconds before said crystallization becomes visually perceptible.

11. A process according to claim 3, wherein said acidic solution has a temperature between 5° C. and 80° C.

12. A process according to claim 3, wherein said acidic solution is prepared by a process comprised of the following steps:

dissolving aspartame in water having a temperature above about 50° C. and a pH greater than about 3 to obtain an aqueous solution of aspartame in water;

adjusting the pH of said aqueous solution of aspartame to less than about 3 by means of an acid to obtain an acidic aqueous solution of aspartame; and cooling said acidic solution of aspartame in water at least about 10° C. while mixing.

13. A process according to claim 12, wherein said pH adjustment is carried out at a temperature between about 50° C. and about 80° C.

14. A process according to claim 12, wherein said acidic solution of aspartame in water is cooled to a temperature below about 70° C.

15. A process according to claim 12, wherein said acidic solution of aspartame in water is cooled to a temperature between about 5° C. and about 35° C.

16. A process according to claim 12, wherein said acidic solution of aspartame in water is cooled in a through-flow heat exchanger.

17. A process according to claim 12, wherein said acid for pH adjustment is an aqueous solution of hydrochloric or sulfuric acid.

18. A process according to claim 3, wherein said acidic solution of aspartame in water is prepared by dissolving an aspartame.HCl salt in water and, optionally, adjusting the pH to between about 1 and about 3.

19. A process according to claim 18, wherein said acidic solution is prepared by dissolving said aspartame.HCl salt in water at a temperature between about 20° C. and about 70° C., and thereafter, cooling said acidic solution.

20. A process according to claim 3, wherein said mixing is carried out at most about 10 seconds before being stopped.

21. A process according to claim 20, wherein said mixing is carried out for at most about 5 seconds.

22. A process according to claim 3, wherein aspartame is allowed to crystallize out of said neutralized solution after said mixing step for between about 2 minutes and about 2 hours without mixing.

23. A process according to claim 3, wherein aspartame is allowed to crystallize out of said neutralized solution after said mixing step at a temperature above about 15° C., after which the mass obtained is cooled further in a crystallizer under forced convection.

24. A process according to claim 3, wherein the crystals obtained are separated from the mother liquor, washed, and dried to a moisture content of between about 1 wt. % and about 6 wt. %.

25. A process according to claim 3, wherein the mixing is stopped at least 4 seconds before crystallization becomes visually perceptible.

26. A process according to claim 3, wherein said mixing is conducted for up 120 seconds.

27. A process according to claim 3, wherein said mixing is conducted for up 120 seconds, and aspartame is allowed to crystallize out of said neutralized solution after said mixing step for between about 2 minutes and about 2 hours without mixing.

28. A process according to claim 3, wherein said neutralized solution has a pH of 4 to 8.

29. A process according to claim 28, wherein said neutralized solution has a pH of 4 to 7.

30. A process according to claim 3, wherein said neutralized solution has a pH of 4 to 8, said mixing is conducted for up 120 seconds, and aspartame is allowed to crystallize out of said neutralized solution after said mixing step for between about 2 minutes and about 2 hours without mixing.

* * * * *